May 14, 1940. A. COUTEAU Plant Pat. 400
ROSE PLANT
Filed Jan. 18, 1940
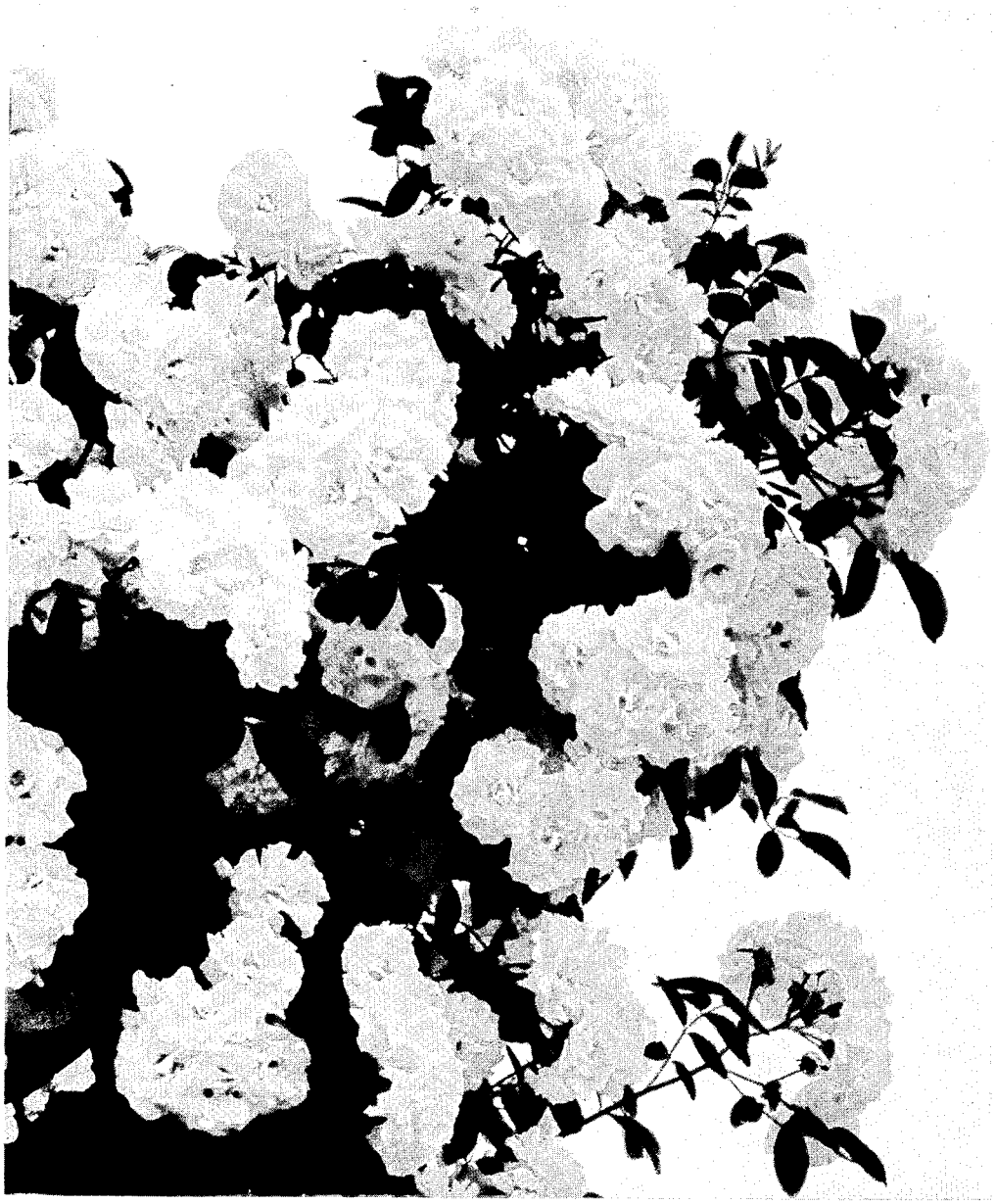
Inventor
Alphonse Couteau
By Robb & Robb
Attorneys Patented May 14, 1940

UNITED STATES PATENT OFFICE

400

ROSE PLANT

Alphonse Couteau, Orleans, France, assignor to Jackson & Perkins Company, Newark, N. Y., a corporation of New York Application January 18, 1940, Serial No. 314,550

1 Claim. (Cl. 47—61)

The present invention appertains to a new and distinct variety of climbing rose plant of the polyantha class, resulting from a cross of a white polyantha × an unknown seedling.

Heretofore, by far the most satisfactory roses among the polyanthas are those having pink and red flowers. For some unknown reason there have been few, if any, varieties of white shades comparable in vigor to the red and pink. This invention, therefore, particularly fulfills a long-felt want in that it is different in this and many respects from any other rose now in cultivation.

Primarily, in habit of growth, the new variety is a climber quite similar to Tausendschön, and this characteristic together with the large clusters of its large white flowers, smooth and glossy foliage, and smooth and almost thornless stems, distinguish it from all other varieties in the polyantha group, and establish a novel combination of characteristics in such a rose.

Another notable feature of my new variety resides in the persistence of its blooming habit in the spring season and occasional remontance in summer and fall.

The plant has been asexually reproduced and its novel characteristics above referred to have been found to be firmly established.

The following is a detail description of the new variety, all references to color being in accord with Ridgway's Color Standard.

Parentage:

*Seed parent.*—White polyantha.

*Pollen parent.*—Unknown.

Classification:

*Botanic.*—Climber.

*Commercial.*—Climber.

*Flower*

(Observations made in the fields and gardens of Jackson & Perkins Company, Newark, New York, in the morning of June 30, 1939.)

Blooming habit: Recurrent—intermittent.

Bud:

*Size.*—Small.

*Form.*—Short with flat top. Is not affected by wet or hot weather.

*Color.*—When sepals first divide—Chamois, Plate 30. When petals begin to unfurl—Marguerite Yellow, Plate 30. When half blown: inside of petals—Marguerite Yellow, Plate 30; reverse of petals—Marguerite Yellow, Plate 30.

*Sepals.*—Serrated and hirsute. Curl back when half blown.

*Calyx.*—Shape—apple. Size—small. Aspect—smooth.

*Peduncle.* — Length — medium. Aspect — prickly. Color—Light Cress Green, Plate 31. Strength—stiff.

*Opening.*—Bud opens well. Is not affected by adverse conditions.

Bloom:

*Size.*—Small.

*Average size when fully expanded.*—Three inches.

*Borne.*—In flat clusters.

*Stems.*—Medium length; normal strength.

*Form.*—When first open—cupped. Permanence—flattens.

*Petalage.*—Double (full but open center). Number of petals under normal conditions—15.

*Color.*—Center of flower—White, Plate 53, with slight tinge of Marguerite Yellow, Plate 30. Outer petals—White, Plate 53, with slight tinge of Marguerite Yellow, Plate 30. Base of petals (aiglet)—Primrose Yellow, Plate 30. Inside of petals—White, Plate 53, with slight tinge of Marguerite Yellow, Plate 30. Reverse of petals—White, Plate 53, with slight tinge of Marguerite Yellow, Plate 30. General tonality from a distance—White.

*Discoloration.*—General tonality at end of first day—White, Plate 53, with Marguerite Yellow, Plate 30. Second day—White, Plate 53. Third day—White, Plate 53.

Petals:

*Texture.*—Thin. Are not affected by wet or hot weather.

*Appearance.* — Inside — satiny; outside — shiny.

*Form.*—Scalloped.

*Arrangement.*—Informal (with "rags" in center). Petaloids in center—few.

*Persistence.*—Drop off cleanly.

*Fragrance.*—Slight. Nature—tea (average hybrid tea scent).

*Lasting quality.*—On the plant—very long. As cut flower—fair.

Genital organs:

*Stamens, anthers.*—Size—small; many. Color—Apricot Yellow, Plate 4. Arrangement—regular around styles.

*Stamens, filaments (threads).*—Size—medium length. Color—Martius Yellow, Plate 4.

*Pollen.*—Apricot Yellow, Plate 4.

*Styles.*—Bunched; medium length; thin.
*Stigmas.*—Color—Martius Yellow, Plate 4.
*Ovaries.*—All enclosed in calyx.

Fruit: Variety is sterile with its own pollen.

*Plant*

Form: Climber.

Growth: Medium, upright.

Foliage: 7 leaflets or more.
*Size.*—Small.
*Quantity.*—Normal.
*Color.*—New foliage: upper side—Light Elm Green, Plate 17; under side—Light Bice Green, Plate 17. Old foliage: upper side—Varley's Green, Plate 18; under side—Rainette Green, Plate 31.
*Shape.*—Lanceolate.
*Texture.*—Upper side—glossy, smooth; under side—smooth. Ribs and veins—light.
*Edge.*—Serrated (saw toothed).
*Serration.*—Single; small.
*Rachis.*—Color—Light Cress Green, Plate 31. Under side—hooked prickles.
*Stipules.*—Medium length; serrated.
*Disease resistance.*—Only slight tendency to black spot.

Wood:
*New wood.*—Color—Bice Green, Plate 17. Bark—smooth.
*Old wood.*—Color—Cress Green, Plate 31. Bark—smooth.

Thorns:
*Thorns.*—Quantity on main stalks from base and on laterals from stalk—few. Form—broad base; hooked downward. Color when young—Mignonette Green, Plate 31. Position—irregular.
*Prickles.*—Quantity on main stalks and on laterals—few. Color—Mars Brown, Plate 15.

Having thus described my new variety, what I claim as new and desire to secure by Letters Patent is:

A new and distinct variety of rose plant of the polyantha group, characterized as to novelty by its climbing habit of growth, its production of large flowers in large clusters and the color of the flowers, its smooth and glossy foliage and the color thereof, its smooth and almost thornless stems, and its persistence of bloom followed by occasional remontance, substantially as shown and described.

ALPHONSE COUTEAU.